United States Patent [19]
Goldowsky

[11] 4,310,930
[45] Jan. 19, 1982

[54] RIGID-VANE ARTIFICAL HEART
[75] Inventor: Michael P. Goldowsky, Valhalla, N.Y.
[73] Assignee: U.S. Philips Corporation, New York, N.Y.
[21] Appl. No.: 97,998
[22] Filed: Nov. 28, 1979
[51] Int. Cl.³ .............................................. A61F 1/00
[52] U.S. Cl. ....................................... 3/1.7; 277/138; 403/288; 417/481
[58] Field of Search ...................... 3/1.7; 417/481, 482, 417/483, 484; 277/101, 12, 138, 5, 6, 133, 134, 168, 185, 189; 403/223, 203, 288

[56] References Cited
U.S. PATENT DOCUMENTS
1,205,338 11/1916 Farley ................................. 417/482
2,988,388 6/1961 Newell ............................... 403/223
4,017,197 4/1977 Farrant ........................... 403/288 X
4,154,546 5/1979 Merrick et al. ................. 403/288 X FOREIGN PATENT DOCUMENTS
2052876 5/1972 Fed. Rep. of Germany ........... 3/1.7
281906 12/1927 United Kingdom ................ 417/483
1210941 11/1970 United Kingdom ................ 417/481

Primary Examiner—Clifford D. Crowder
Attorney, Agent, or Firm—Marc D. Schecter

[57] ABSTRACT

A rigid-vane artificial heart pump includes a vane shaft which extends from the gear box into the blood pumping chamber and a torsion seal for hermetically sealing the gear box from the pumping chamber so as to prevent contamination of blood. Check valves are provided to control the blood flow direction and to determine the pump's mode of operation.

15 Claims, 8 Drawing Figures

RIGID-VANE ARTIFICAL HEART

BACKGROUND OF THE DISCLOSURE

The invention relates to artificial heart pumps; and more particularly, to an oscillating vane-type pump having hermetic sealing between the motor and vane cavity.

The invention may be used in artificial heart pumps of the type which are implantable within the body of a person whose heart is being assisted or replaced by the artificial heart pump.

Artificial heart pumps, as heretofore known, have used elastomeric pumping diaphragms for exerting pressure on the blood to be pumped. Elastomeric components have been used exclusively till now because they eliminate blood damaging seals and because they simplify pump control by inherently operating under Starling's Law. The useful lifetime of such artificial heart pumps, however, is relatively short. The elastomeric diaphragms, which are subjected to extreme stress and distortion in the operation of such pumps, have characteristically been the life-limiting elements of such pumps. These known pumps utilize only one power stroke and one filling stroke per cycle.

It would be advantageous to provide an artificial heart pump which has a relatively long useful lifetime and which incorporates seals which do not excessively damage blood cells.

It would also be advantageous to provide a pump which has two power strokes per cycle, each one occurring during a simultaneous filling stroke for the next power stroke.

SUMMARY OF THE INVENTION

An object of the invention is to provide an artificial heart pump without an elastomeric pumping diaphragm, thereby providing a relatively longer useful lifetime for the pump.

A further object of the invention is to provide a vane-type artificial heart pump having seals which do not excessively damage blood cells.

These and other objects and advantages of the invention will be more fully described below.

According to the invention, an angularly oscillating vane-type artificial heart pump includes a torsion seal. Such a pump includes a rigid housing having walls defining a pumping chamber with at least one intake port and one outlet port. A vane shaft, having two ends and a longitudinal axis therethrough, is pivotally mounted in the housing about its longitudinal axis, and has one end thereof extending into the pumping chamber through an opening in a wall of the pumping chamber. A rigid vane is mounted on the vane shaft in the pumping chamber so that the vane will pivot with the vane shaft on the longitudinal axis. The vane need only pivot through a limited angle and it is preferably made to pivotally oscillate through this angle in order to create the desired pumping action. The dimensions of the vane are preferably chosen such that as the vane pivots, through a desired angle, the vane will not contact any of the walls of the pumping chamber, thus forming a clearance seal. In order to effect a fluid-tight seal between the vane shaft and the pumping chamber wall, the torsion seal is provided, made of a tube-shaped resilient sealing material having two ends. The torsion seal is mounted substantially coaxially around the vane shaft and has one end being sealed fluid-tight to the vane shaft, and the other end being sealed fluid-tight to the wall through which the vane shaft extends.

More generally, a torsion seal according to the invention may be used to seal the space between any longitudinal member and a wall surrounding such a member, where the wall and member are moving in relative pivotal motion through a limited angular displacement. Such a torsion seal may be used in pumps, motors, valves and other devices having this type of structure.

According to another aspect of the invention, the vane divides the pumping chamber into two ventricles of variable volume and each ventricle has both an intake port and an outlet port. A check valve is provided in each port to allow fluid to flow through each port in one direction only. By virtue of this construction, fluid is pumped on both the forward and return strokes of the vane. Thus, there are two power strokes of the pump per cycle, each one occurring simultaneously with a filling stroke for the opposite ventricle.

According to yet another aspect of the invention, one ventricle has an intake port and the other an outlet port. One check valve is provided in the outlet port and another in the vane. By this configuration, unidirectional assist pumping is achieved with only one power stroke per cycle.

DESCRIPTION OF THE PREFERRED EMBODIMENTS

General Construction

Figure 1:
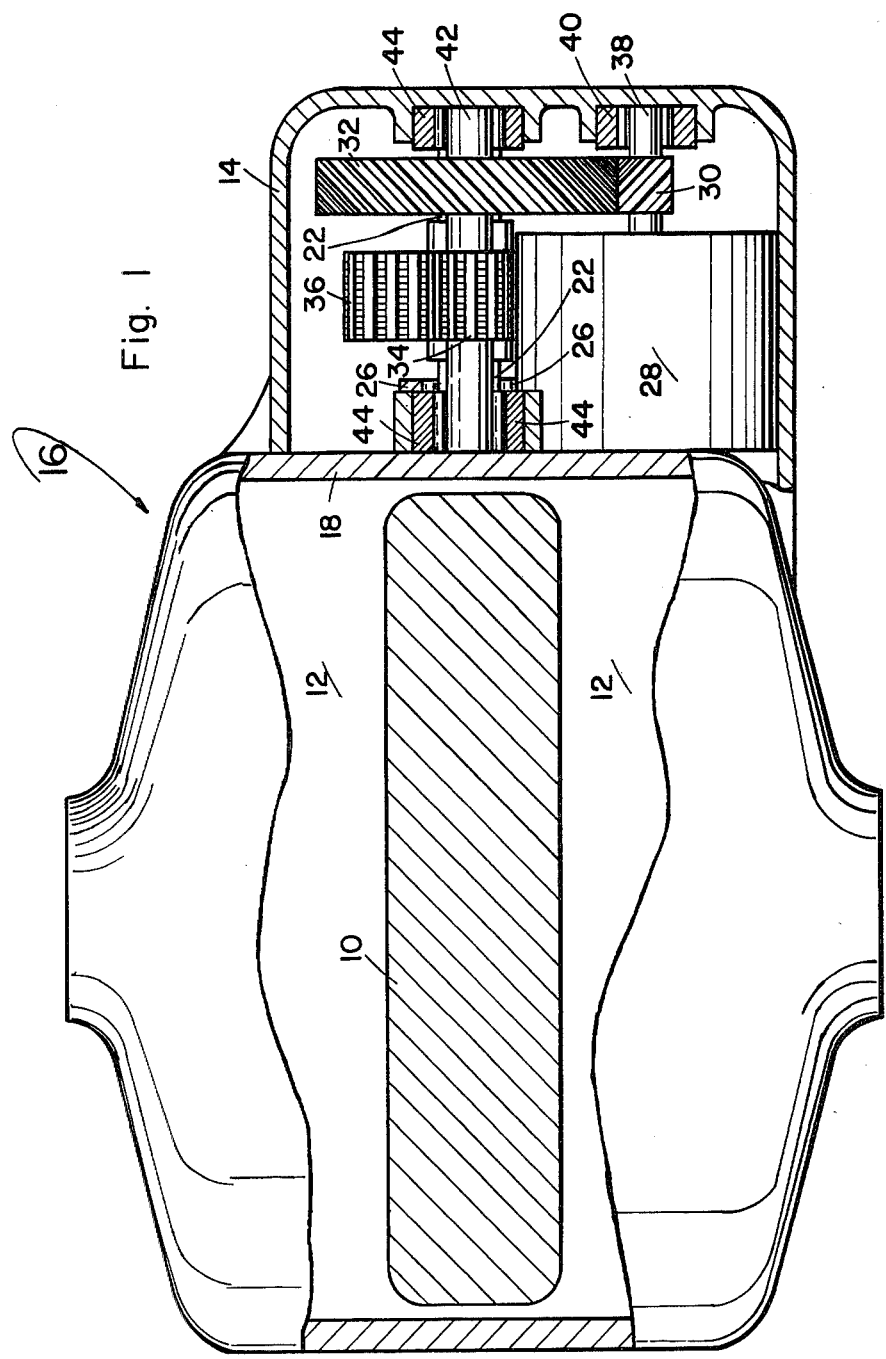
FIG. 1 is a top view, partly in section and partly cut away, of an artificial heart pump according to the invention.
Figure 2:
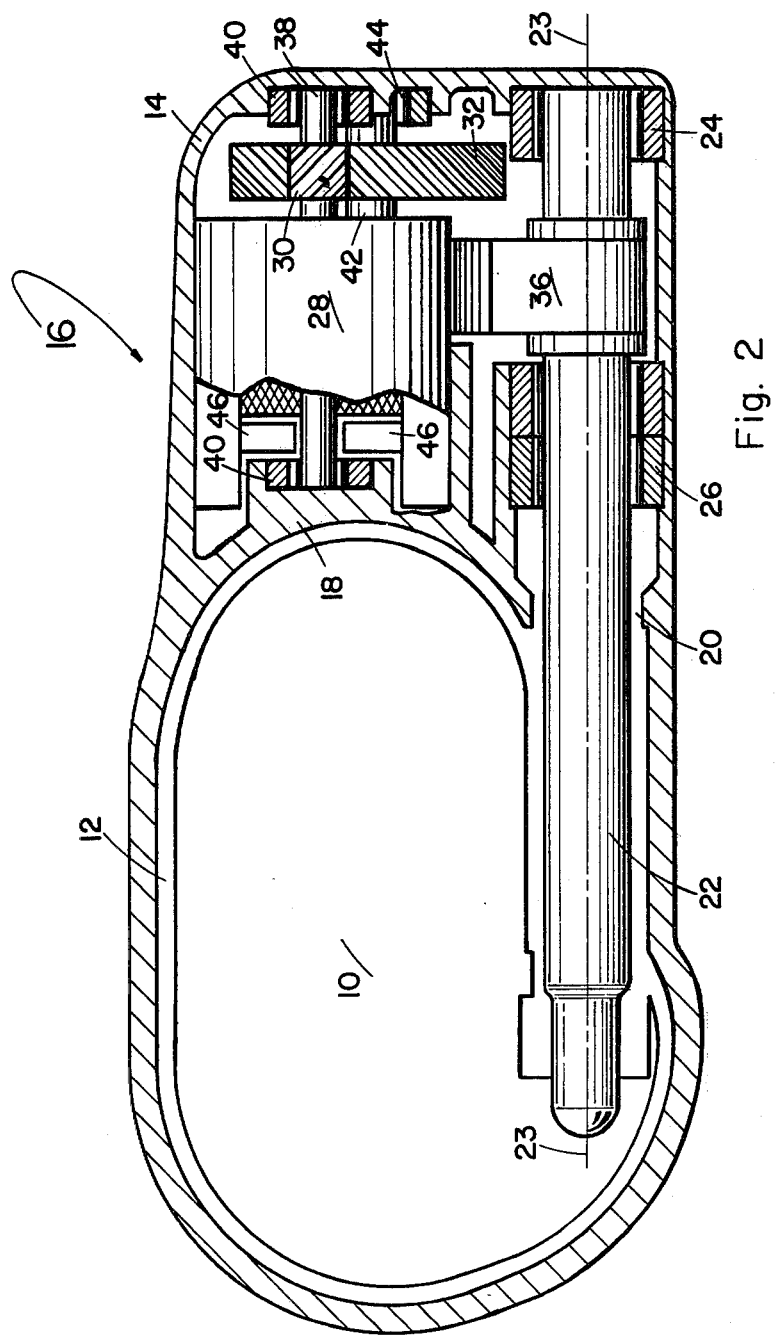
FIG. 2 is a side view, partly in section and partly cut away, of the artificial heart pump of FIG. 1.
Figure 3:
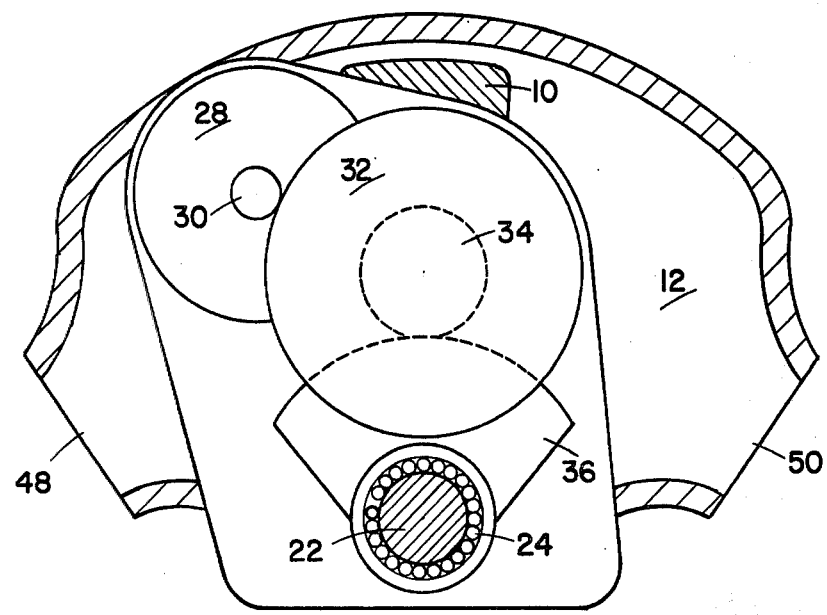
FIG. 3 is a front view, partly in section and showing some elements in phantom, of the artificial heart pump of FIG. 1.

A rigid vane artificial heart pump is shown in FIGS. 1-3. The vane 10 is mounted in a pumping chamber 12. Adjacent to pumping chamber 12 is a gear box 14. Pumping chamber 12 and gear box 14 make up the artificial heart pump housing 16. In the housing 16, pumping chamber 12 and gear box 14 are separated by a wall of the pumping chamber, partition 18. Partition 18 is provided with an opening 20 (FIG. 2) through which a vane shaft 22 passes from gear box 14 into pumping chamber 12.

Vane shaft 22 is cantilevered in housing 16 on bearings which are located solely in gear box 14. In this way, only one seal (FIG. 7) need be provided between vane shaft 22 and partition 18, so as to prevent fluid flow between pumping chamber 12 and gear box 14. Vane shaft 22 has a longitudinal axis 23 through its two ends, around which it pivots.

Vane 10 is made of a rigid material and is preferably either keyed to vane shaft 22 or is mounted on splines (neither shown) on one end of vane shaft 22 so that vane 10 will pivot with vane shaft 22 around the longitudinal axis 23. A set screw or the like (not shown) should be provided to prevent vane 10 from sliding off vane shaft 22.

An advantage of using a rigid vane pump lies in the ability to use titanium for internal surfaces. This material (and also pyrolytic carbon) are two of the best known materials today for minimizing the development of thromboli (blood clots) over a long term. The interior of pumping chamber 12 may be lined with the same material.

As can be seen in FIG. 2, the other end of vane shaft 22, in gear box 14, is mounted in a needle bearing 24. In the preferred embodiment, the peak load on this bearing is 40 newtons (9.1 pounds), its dynamic capacity is 2600 newtons (580 pounds). A set of back-to-back tapered roller bearings 26 are positioned a substantial distance away from the needle bearing 24 in gear box 14. In this way, the three bearings easily support the moment imposed on the cantilevered vane shaft caused by the pressure of the blood and the weight of the vane 10. The tapered bearings are preloaded to precisely position the vane in the pumping chamber, described further below.

A DC motor 28 is also mounted in gear box 14. Motor 28 is preferably a low inertia DC motor, so as to allow the motor to reverse direction and quickly accelerate to its nominal speed, with a nominal speed of 100 revolutions per second (6000 rpm). In the prototype model a brushless D.C. motor, having a samarium cobalt armature and a volume of 16 cubic centimeters (1 cubic inch), was used. A gear train is provided in the gear box for coupling the motor 28 to the vane shaft 22 and for reducing the speed of rotation of the vane to 0.83 revolutions per second (50 rpm). This gear train includes Evoloid (trademark) motor pinion 30, Evoloid (trademark) gear 32, spur gear pinion 34, and vane drive gear segment 36. The Evoloid-type helical spur gears provide a high reduction ratio with high efficiency and long life.

Motor pinion 30 is mounted on motor shaft 38 to rotate with the motor shaft. Motor shaft 38, is mounted on motor bearings 40 in gear box 14. In order to provide an immediate 30 to 1 reduction in speed, gear 32 is provided, on intermediate shaft 42 which is mounted in gear box 14 on bearings 44, to mesh with motor pinion 30.

Also attached to intermediate shaft 42 is spur gear pinion 34. Gear 32 and spur gear pinion 34 rotate at the same velocity due to their rigid connections to intermediate shaft 42.

Vane drive gear segment 36 is rigidly mounted to vane shaft 22 at a location between needle bearing 24 and tapered roller bearings 26. Vane drive gear segment 36 is meshed with spur gear pinion 34 to provide a final 4 to 1 speed reduction.

The pinion 30/gear 32 reduction ratio of 30 to 1 is necessary in the first stage to minimize the reflected inertia of the gear train since the motor must accelerate to speed in only 0.025 seconds. In addition, the approach taken in designing a long life, quiet and reliable speed reducer was to oversize the bearings and to immerse them in oil of a viscosity which ensures development of a hydrodynamic film. The final 4 to 1 speed reduction is accomplished using a large diameter pinion with a long face for minimal wear.

Since the gear box is nearly filled with oil, two hermetic magnetic fluid seals 46 may be provided to keep the magnetic lubricating oil out of the motor. The combined power consumption in the prototype of both magnetic seals at 83.3 revolutions per second (5000 rpm) is only 0.043 watts and their pressure capability is 10 kPa (15 psi). Calculations have shown that if the oil were permitted to reach the armature air gap, the viscous loss would amount to 2.3 W. Thus, the use of magnetic seals can save a significant amount of power. For simplicity, however, a light grease lubricant may be used in the gear box and these seals may be eliminated.

To develop blood pumping action, the vane 10 is pivotally oscillated back and forth, preferably through 90°, by driving low inertia DC motor 28 first in one direction and then in the other. Between the vane 10 and the walls of pumping chamber 12 is a gap, or clearance seal. The clearance seal is preferably 100 microns (0.004 inches). The vane 10 should not contact the walls of chamber 12 at any time throughout its range of rotation. Such a clearance seal will not cause excessive damage to blood cells due to the action of the artificial heart pump. Pumping chamber 12 has one or more intake ports and outlet ports to accommodate blood flow. One or more check valves, for example Bjork-Shiley type valves, are provided, as further discussed below, in order to ensure that the blood flow is in the proper direction.

Flow Direction Control

Figure 4:
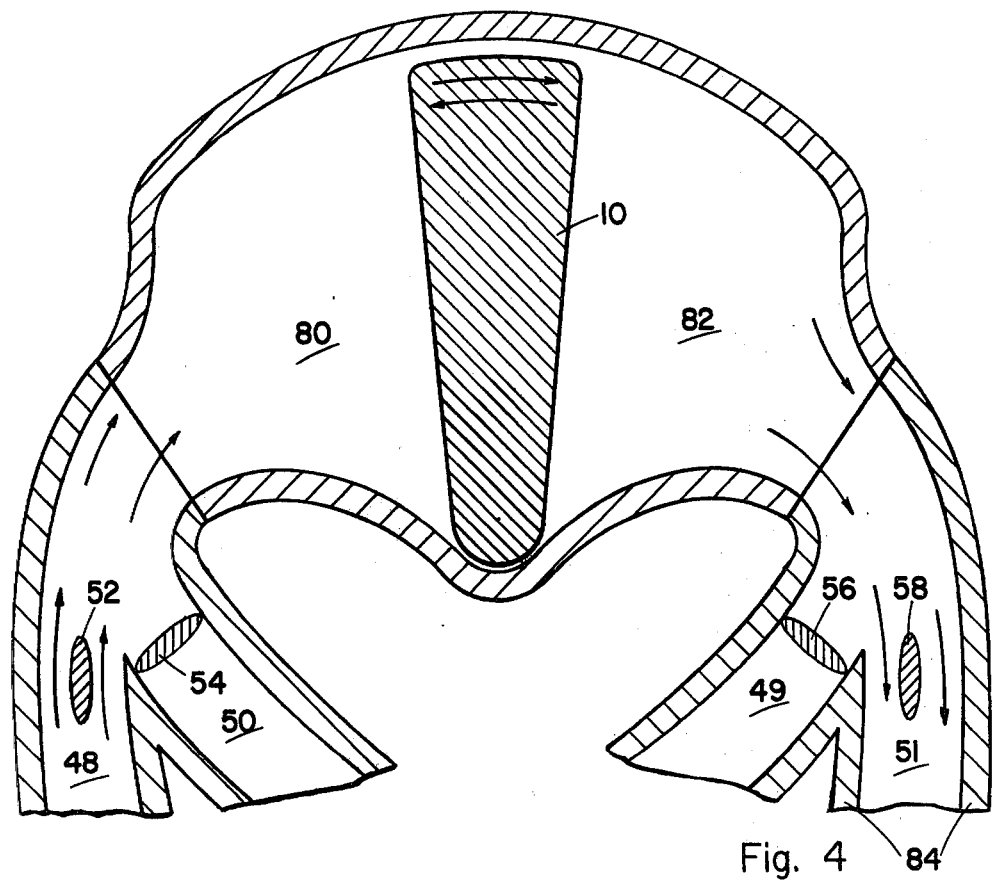
FIG. 4 is a schematic representation of a rigid vane type artificial heart pump according to one embodiment of the invention.

The preferred configuration for the blood flow direction control system is shown in FIG. 4. In this embodiment the pump functions as a total heart replacement. Vane 10 divides the pumping chamber into two ventricles of variable volume, left ventricle 80 and right ventricle 82. Each ventricle has both an inlet port, 48 or 49, and an outlet port 50 or 51. Each port is provided with a check valve 52, 54, 56 and 58, schematically shown in FIG. 4. As seen in this figure, during the portion of a cycle when the rigid vane 10 is pivoting clockwise, check valves 52 and 58 are open to permit blood flow from intake port 48 into the left ventricle thereby filling the left ventricle, at the same time that the vane 10 forces blood out of the right ventricle through outlet port 51. Check valves 54 and 56 remain closed. Conversely, during the part of the cycle when rigid vane 10 is pivoting counterclockwise, check valves 54 and 56 are open to permit blood flow and check valves 52 and 58 are closed. Accordingly, blood will flow from intake port 49 into the right ventricle, thereby filling the right ventricle, and rigid vane 10 will force blood from the left ventricle through outlet port 50.

Due to the well known requirement that the right side of the human heart must pump less blood (to the lungs) than the left side (to the rest of the body), in this embodiment check valve 58 preferably leaks approximately 15% when "closed" to allow blood to flow back into the right ventricle 82 on the counter-clockwise stroke. Alternatively, check valve 58 need not leak at all if an extra check valve is provided in vane 10 to allow some leakage during the clockwise stroke, as described below. (See, FIG. 4A for a check valve in the vane.)

Figure 4A:
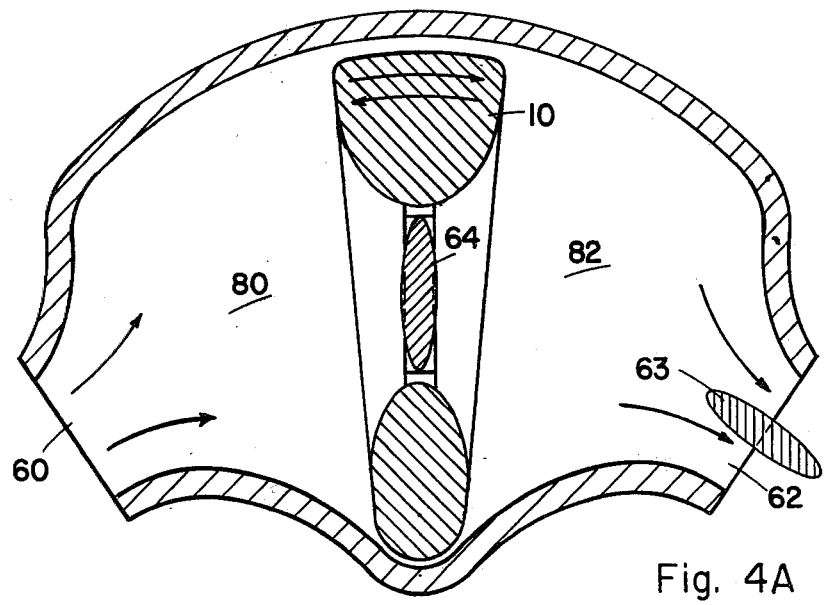
FIG. 4A is a schematic representation of a rigid vane type artificial heart assist pump according to another embodiment of the invention.

In an alternate embodiment, shown in FIG. 4A, the artificial heart pump may be used as an assist device rather than as a heart replacement. In the assist device, pumping chamber 12 is provided with a single intake port 60 at one end of the chamber and with a single outlet port 62 at the opposite end. Instead of providing check valves in both ports, a single check valve 63 is provided in outlet port 62 and a single check valve 64 is provided in vane 10. During the portion of the stroke when the vane 10 is pivoting clockwise, check valve 64 remains closed, blocking fluid flow therethrough, and fluid will be drawn into the left ventricle from intake port 60, thereby filling the left ventricle. At the same time, check valve 63 is open and rigid vane 10 then forces blood out of the right ventricle through outlet port 62. On the return stroke, when rigid vane 10 is pivoting counterclockwise, check valve 64 opens thereby allowing fluid flow therethrough, so that blood in the left ventricle will travel to the right ventricle instead of being forced back through intake port 60, and check valve 63 is closed to prevent blood from flowing back into the right ventricle via outlet port 62.

It is apparent that a rigid vane heart, according to the total heart replacement embodiment, is advantageous because a single pumping chamber is shared by both sides of the heart so that the device volume is no greater than that of the assist pump, except for the additional check valves.

Clearance Seal

Figure 5:
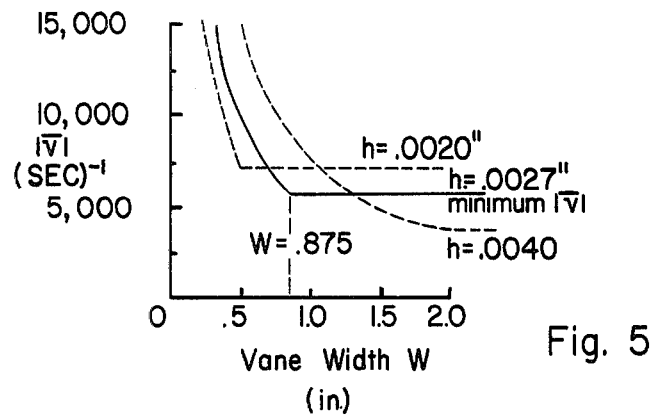
FIG. 5 is a plot of the blood shear rate parameter versus vane width, for various gaps, or clearances, between the vane and the walls of the pumping chamber.

In all embodiments of the artificial pump according to the invention, it is important to optimize the distance between the vane and the housing throughout the complete cycle of the vane, and it is also important to optimize the vane geometry. The clearance seal concept by itself, namely the use of a rigid blood pumping surface which does not contact the walls of the pumping chamber, has been shown in actual tests to produce little blood cell damage. Nevertheless, blood damage may be further minimized if the vane and pumping chamber geometry are chosen properly. FIG. 5 is a graph showing a blood shear rate parameter versus vane width for various gaps h. This graph shows that when a vane width of 2.22 centimeters (0.875 inches) is selected, an absolute minimum value for the shear rate parameter occurs at a gap of 0.0068 centimeters (0.0027 inches). For manufacturing tolerance reasons, however, a range in gap is desirable of up to 0.01 centimeters. The side of the vane, at the extreme end of a stroke, should be spaced from the housing by a distance which is relatively much larger than the size of the "gap".

A shear rate parameter, $|\bar{v}|$, in a gap in an artificial heart pump according to the invention, may be defined as one half the sum of the shear rate at the surface of the pumping chamber plus the shear rate at the surface of the vane tip. The shear rates at these surfaces are chosen because it is assumed that blood damage is produced primarily at these surfaces. For a given gap clearance h* and a given vane width $$W^* = \frac{\Delta P h^{*2}}{2\mu u_o}, \; |\bar{v}| \text{ can be given by the expressions}$$

$$|\bar{v}| = \frac{u_o}{h} \text{ for } h \leq h^* \text{ and } W \geq W^*$$

$$|\bar{v}| = \frac{h \Delta P}{2\mu W} \text{ for } h > h^* \text{ and } W < W^*$$

where
W = vane width (in.)

h = gap clearance (in.)
$\Delta P$ = pressure across vane (psi)
$|\bar{v}|$ = shear rate parameter (L/sec.)
$u_o$ = vane tip velocity (in L/sec)
$\mu$ = blood viscosity at a given shear rate (lb-sec/in$^2$)

Thus, to minimize $|\bar{v}|$, for a given vane width W, the gap clearance h should be chosen such that $$h = \sqrt{\frac{2\mu u_o W}{\Delta P}}. \text{ (See, FIG. 5)}$$

During operation of the artificial heart pump, the blood velocity in the vane-housing gap, due to back-flow, may be substantial. This blood must, upon leaving the gap, decelerate and mix with the pumping chamber blood which is essentially at rest. By using the proper vane contour, the blood can be made to slow down at constant deceleration. This "optimal" condition minimizes inertial forces on the red cells and should produce negligible turbulence in the exiting blood. The same conditions also apply to blood entering the gap, which is accelerated. In both cases, the more uniform the acceleration or deceleration, the less damage to blood cells which will occur. Calculations have shown that the optimum vane profile is governed by the equation $$x = \frac{h^4 \Delta P^2}{|a| \, 288 \, \mu^2 \, W^2} \left[ 1 - \frac{1}{(y/h + 1)^2} \right]$$

so as to allow the exiting blood to uniformly accelerate and decelerate. This curve is plotted in FIG. 6 which is a partial cross-sectional view of the vane in a plane which is perpendicular to the axis of rotation. The central portion of the top of the vane is substantially flat and parallel to the surface of the adjacent wall of the housing. An x-y coordinate system is defined having the x-axis parallel to the central portion of the top of the vane and having an origin at the point where the top of the vane begins to curve away from the wall of the housing. The remaining nomenclature is defined as follows:
a = blood acceleration (in/sec$^2$)
h = vane gap (in)
W = vane width along leakage flow (in)
P = pressure across vane (psi)
u = effective blood viscosity (lb-sec/in$^2$)

Figure 6:
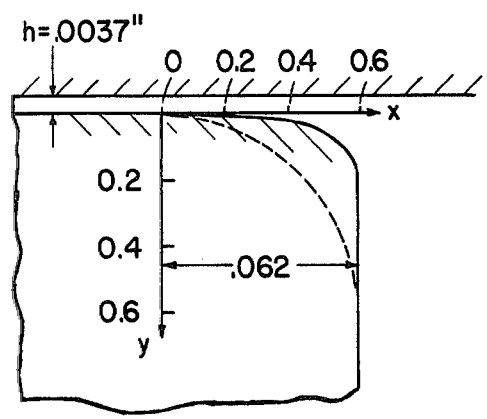
FIG. 6 is a schematic illustration of two cross-sectional geometries of the rigid vane through a plane which is perpendicular to the axis of the vane shaft.

In FIG. 6, it should also be understood that preferably the vane profile is identical in any parallel cross-sectional plane, and the profile on the left side of the vane is a mirror image of the right profile shown.

The function plotted in FIG. 6, where the vane has been enlarged, results when a deceleration length of 0.157 centimeters (0.062 inches) is chosen. The blood then has only 4% of its initial velocity at the vane exit. The dotted curve is an arc of a circle having a radius of 0.157 centimeters. A vane having the latter shape induces 300% more body force on blood cells than does the optimized design.

Torsion Seal

Figure 7:
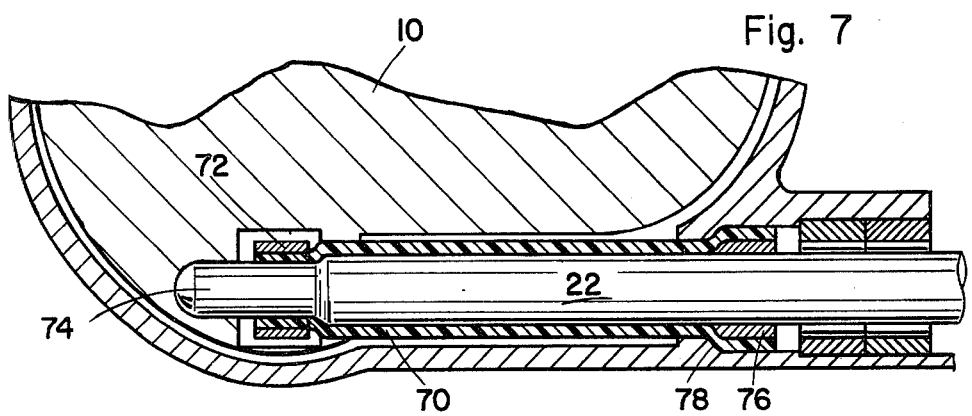
FIG. 7 is an enlarged view, partly in section, of the torsion seal of FIG. 2.

In order to prevent the contamination of blood with lubricating oil from the gear box, a hermetic torsion seal 70 is provided. (FIG. 7.) As can be clearly seen in FIG. 7, the torsion seal 70 comprises a tube-shaped resilient sealing material having two open ends. Torsion seal 70 is mounted substantially coaxially around vane shaft 22 and has one end sealed fluid-tight to the vane shaft, and the other end sealed fluid-tight to the surrounding wall of pumping chamber 12.

A suitable resilient, sealing material for use in manufacturing a torsion seal is a polyurethane compound, such as Avcothane Q (trademark) or Avcothane 51 (trademark) or Biomer (trademark). Fabrication of the tube shaped seal could be performed by methods such as spray or dip coating an appropriate mandril in a clean room environment, or by press forming. Curing occurs at ambient temperatures in about 16 hours. To compensate for shrinkage, the outside diameter of the mandril should be about 5% greater than the desired tube diameter. It is essential that the surface of the mandril be smooth for maximum fatigue resistance on the inside diameter of the seal. Likewise, in order to prevent blood clots from occurring on the outer surface of the seal, imperfections of the size of a small dust particle or larger should not be present on this interface. The mandril should preferably be made of stainless steel. It has been found feasible to freeze the seal in liquid nitrogen and then accurately machine its inside diameter and outside diameter to the tolerances required since molding alone is not sufficiently accurate.

The fastening of torsion seal 70 to vane shaft 22 may be accomplished by the use of a thin clamping band 72 of titanium. In order to prevent seal 70 from moving axially along vane shaft 22, vane shaft 22 is provided with a reduced diameter portion 74 on which clamping band 72 is mounted. Additionally, splines may be molded on the inside diameter of the seal to mate with matching ones in the shaft beneath the bond.

To fasten the other end of torsion seal 70 to the walls of pumping chamber 12 (partition 18 being one of the walls), either the same proposed clamping method may be employed (not shown) or an internal sleeve 76 can be used. As shown in FIG. 7, sleeve 76 causes the end of torsion seal 70 to expand into a flared groove 78 in the wall of the pumping chamber, thus fastening the end of torsion seal 70 to the wall. The seal could also be bonded to a metal sleeve which is screwed in place in the pump housing.

Other methods may be used for fastening the torsion seal 70 to the vane shaft 22 and the walls of pumping chamber 12, such as directly bonding the torsion seal 70 to these surfaces. Epoxy resins have been found to work well in bonding to titanium alloys.

In order to provide lubrication between torsion seal 70 and vane shaft 22, SAE 30 lubricating oil or a silicon grease is placed on shaft 22 at the time of assembly of the seal. Seal 70 is then installed over shaft 22 and is then clamped in place. Thus, oil fills the close fitting gap (of at most 100 microns (a few thousandths of an inch)) located between the shaft 22 and the seal 70. In addition, shaft 22 is preferably made with a Teflon (TM) coating.

Although the dimensions of torsion seal 70 may vary greatly, depending upon the particular application of the seal, in the model artificial heart pump which has been built, a seal was manufactured having a 8 millimeter (5/16th inch) inside diameter and a 0.16 centimeter (1/16th inch) wall thickness. If the wall thickness is too small, the walls of the tube may buckle in operation. The seal was made 2.54 centimeters (1 inch) long to reduce the induced strain or percent stretch of the seal when the ends thereof are pivoted 45° with respect to each other. It can be appreciated that the strain on the seal will decrease as the length of the seal is increased. The use of a relatively long seal is accomplished by cantilevering the vane, as described above. An added benefit of cantilevering is the fact that only one seal is required.

The possibility of oil diffusion through the material of torsion seal 70, even though it is quite thick, has been recognized. According to the Avco Corporation, Avcothane (Trademark) is believed to shed mineral oil lubricant especially if it is press-formed at 343–353 K (70°–80° C.). Pressed films have substantially reduced porosity over the cast types. If this method of fabrication does not prove to offer sufficient resistance to diffusion, then a thin layer of Saran (Trademark) film material (vinylidene chloride) may be laminated into the seal wall. Such a film is impervious to mineral oil and will bond to Avcothane (Trademark). In addition, such a film possesses not only high tensile strength, typically 3.45 MPa (5,000/psi), but for this application has a sufficient elongation of typically 25%.

Pump Motor Control

In order to control the pumping of blood by an artificial heart pump according to the invention, many different control systems could be used. For a heart assist pump, the simplest system synchronizes pumping with the natural heartbeat.

For controlling a total heart replacement pump, two possible systems are proposed. The first is to operate the pump as a variable volume device. By monitoring the left ventricle filling pressure, vane stroke volume and speed are completely determinable by Starling's Law which relates blood flow rate requirements to the filling pressure at the heart inlet. The primary concern, in operation of the pump, is to be sure that the filling pressure does not become negative with respect to atmospheric pressure. Using feedback control from a pressure transducer, left ventricle filling pressure can be maintained between prescribed limits. To compensate for atmospheric pressure variations, either a single pressure transducer may be used which measures gauge pressure or an absolute pressure transducer may be used with a second pressure sensor which is located externally.

The second system is to run the pump at constant stroke volume. Flexible sacks (i.e. chambers with flexible walls) would be located at the outlet ports of the pump to stabilize filling pressure. The flexible walls would be, for example, walls 84 in FIG. 4. This method can also be used in place of the leaky outlet valve in the right ventricle to compensate for the left ventricle.

Modifications and variations of the above-described embodiments of the invention will occur to those with ordinary skill in the art. For example, the torsion seal could be sealed to the vane shaft inside the gear box and sealed to the housing in the pumping chamber. These and other such modifications are intended to be within the scope of the claims, below.

What is claimed is:
1. An artificial heart pump comprising:
a rigid housing having walls defining a pumping chamber with at least one intake port and one outlet port;
a vane shaft, having two ends and a longitudinal axis therethrough, pivotally mounted in the housing about its longitudinal axis, and having one end thereof extending into the pumping chamber through an opening in a wall of the pumping chamber;

a rigid vane, mounted on the vane shaft in the pumping chamber so that the vane will pivot with the vane shaft about the longitudinal axis; and a torsion seal, for effecting a fluid-tight seal between the vane shaft and the wall of the pumping chamber through which the vane shaft extends, said torsion seal comprising a tube-shaped resilient material having two ends and being mounted substantially coaxially around the vane shaft, one end of said tube being sealed fluid-tight to the vane shaft and the other end being sealed fluid-tight to the wall of the pumping chamber through which the vane shaft extends, thereby hermetically sealing the pumping chamber.

2. An artificial heart pump, as claimed in claim 1, wherein the housing further comprises a gear box, located outside the pumping chamber, into which the other end of the vane shaft extends, and further comprising:

a motor, mounted in the gear box; and a gear train, mounted in the gear box, for coupling the motor to the vane shaft;

whereby the torsion seal effects a fluid-tight seal between the pumping chamber and the gear box.

3. An artificial heart pump, as claimed in claim 2, wherein the vane shaft is mounted on bearings in the gear box, and wherein the torsion seal is at least one inch long.

4. An artificial heart pump, as claimed in claim 2, wherein the vane divides the pumping chamber into two ventricles of variable volume, and where each ventricle is provided with an intake port and an outlet port, each of said ports having check valves for allowing fluid to flow therethrough substantially in one preselected direction only.

5. An artificial heart pump as claimed in claim 4, wherein only the check valves of the intake port of the left ventricle and of the outlet port of the right ventricle are open when the vane pivots toward the right ventricle, and only the check valves of the intake port of the right ventricle and of the outlet port of the left ventricle are open when the vane pivots toward the left ventricle.

6. An artificial heart pump, as claimed in claim 4, where the vane is provided with a check valve to allow fluid to flow therethrough in one preselected direction only.

7. An artificial heart pump, as claimed in claim 4, wherein the check valve in the outlet port on one side of the pump leaks, when closed, approximately 15% more than the other check valves leak when closed.

8. An artificial heart pump, as claimed in claim 4, further comprising a chamber having flexible walls, said chamber having an inlet fluidly connected to an outlet port of the pump, for stabilizing pressure output from the pump.

9. An artificial heart pump, as claimed in claim 2, wherein the vane divides the pumping chamber into two ventricles of variable volume, wherein each ventricle has only one port, the port of one ventricle being the intake port and the port of the other being the outlet port, and wherein the vane is provided with a check valve to allow fluid to flow therethrough in one preselected direction only and the outlet port is provided with a check valve to allow fluid to flow therethrough, out of the pump only.

10. An artificial heart pump, as claimed in claim 2, wherein the clearance between the vane and the walls of the pumping chamber is approximately 0.004 inches, throughout the entire range of rotation of the vane.

11. A torsion seal for effecting a fluid-tight seal between a longitudinal member and a wall surrounding such member, where the member and the wall are moving in relative pivotal motion through only a limited angular displacement, comprising a tube-shaped resilient sealing material having two ends, said tube being mounted substantially coaxially around the longitudinal member, and having one end of said tube being sealed, fluid-tight, and fastened to the longitudinal member, and the other end being sealed, fluid-tight, and fastened to the surrounding wall, said tube ends being fastened such that the tube-shaped resilient sealing material twists as the longitudinal member pivots relative to the surrounding wall.

12. A torsion seal as claimed in claim 11, wherein the tube-shaped resilient sealing material further comprises a thin layer of lubricant impervious material.

13. A torsion seal as claimed in claim 12, wherein the lubricant impervious material is vinylidene chloride.

14. A torsion seal as claimed in claim 11, 12, or 13, wherein the ends of the tube are fastened to the longitudinal member and to the surrounding wall, respectively, by the use of epoxy resin.

15. An artificial heart pump as claimed in claim 1, 2, 3, 4, 5, 6, 7, 8, 9, or 10, wherein the ends of the tube are fastened to the vane shaft and to the wall of the pumping chamber, respectively, said tube ends being fastened such that the tube-shaped resilient material twists as the vane shaft pivots relative to the pumping chamber wall.

* * * * *

UNITED STATES PATENT AND TRADEMARK OFFICE
CERTIFICATE OF CORRECTION

PATENT NO. : 4,310,930
DATED : January 19, 1982
INVENTOR(S) : MICHAEL P. GOLDOWSKY It is certified that error appears in the above—identified patent and that said Letters Patent is hereby corrected as shown below:

On the title page

Assignee should be changed from "U.S. Philips Corporation" to --North American Philips Corporation--.

Signed and Sealed this

Seventh Day of June 1983

[SEAL]

Attest:

DONALD J. QUIGG

Attesting Officer

Acting Commissioner of Patents and Trademarks